(12) United States Patent
Campbell, Jr. et al.

(10) Patent No.: US 7,044,931 B2
(45) Date of Patent: May 16, 2006

(54) SYRINGE WITH RETRACTABLE NEEDLE ASSEMBLY

(75) Inventors: Vance D. Campbell, Jr., Oceanside, CA (US); Joseph Nebolon, San Diego, CA (US); Robert D. Adams, Shamong, NJ (US); Patrick Chng, Singapore (SG); April Marano-Ford, Manhattan Beach, CA (US)

(73) Assignee: Hypoguard USA Inc., Edina, MN (US)

( * ) Notice: Subject to any disclaimer, the term of this patent is extended or adjusted under 35 U.S.C. 154(b) by 365 days.

(21) Appl. No.: 10/345,901

(22) Filed: Jan. 16, 2003
(Under 37 CFR 1.47)

(65) Prior Publication Data

US 2004/0006314 A1    Jan. 8, 2004

Related U.S. Application Data

(63) Continuation of application No. PCT/US00/33897, filed on Dec. 13, 2000.

(51) Int. Cl.
*A61M 5/315* (2006.01)

(52) U.S. Cl. ..................................... 604/110

(58) Field of Classification Search ............... 604/110, 604/198, 195, 192, 263
See application file for complete search history.

(56) References Cited

U.S. PATENT DOCUMENTS

| 4,921,486 A | * | 5/1990 | DeChellis et al. ........... 604/110 |
| 4,927,414 A | * | 5/1990 | Kulli ........................... 604/110 |
| 5,167,641 A | * | 12/1992 | Schmitz ........................ 604/196 |
| 5,211,628 A |   | 5/1993 | Marshall ...................... 604/110 |
| 5,484,421 A |   | 1/1996 | Smocer ........................ 604/195 |
| 5,693,023 A |   | 12/1997 | Adams ........................ 604/195 |
| 5,782,804 A |   | 7/1998 | McMahon .................... 604/110 |
| 6,050,977 A |   | 4/2000 | Adams ........................ 604/195 |
| 6,409,701 B1 | * | 6/2002 | Cohn et al. .................. 604/110 |
| 6,676,641 B1 |   | 1/2004 | Woodard, Jr. et al. ...... 604/187 |

FOREIGN PATENT DOCUMENTS

| WO | WO 01/41843 | 6/2001 |
| WO | WO 02/066097 | 8/2002 |

OTHER PUBLICATIONS

U.S. Appl. No. 10/190,441, filed Jul. 2, 2002 to Woodard et al.
U.S. Appl. No. 10/247,781, filed Sep. 16, 2002, to Montalvo et al.
U.S. Appl. No. 10/450,573, filed 1/7/200s to Field et al.

* cited by examiner

*Primary Examiner*—Sharon Kennedy
(74) *Attorney, Agent, or Firm*—Connolly Bove Lodge & Hutz LLP

(57) ABSTRACT

A disposable, single use syringe comprised of a hollow body, a retractable needle assembly positioned in the hollow body, and a plunger assembly in the hollow body. The plunger assembly includes an elongated frame portion including at least one guide track between its ends. A retraction member is releasably secured to one end of the frame and a catch member, including a catch element, is positioned with a guide configured to travel in the plunger frame guide track. An elastic member extends between the retraction member and the catch member. A retention assembly depends from the opposite end of the plunger frame and is configured to receive and secure the catch element and thereby tension the elastic member. The needle assembly and the retraction member have complimentary mating members, whereby the tension on the elastic member is released and the injection means is drawn into the hollow body after the needle assembly and the retraction member mate. A method of manufacture is also provided.

54 Claims, 11 Drawing Sheets

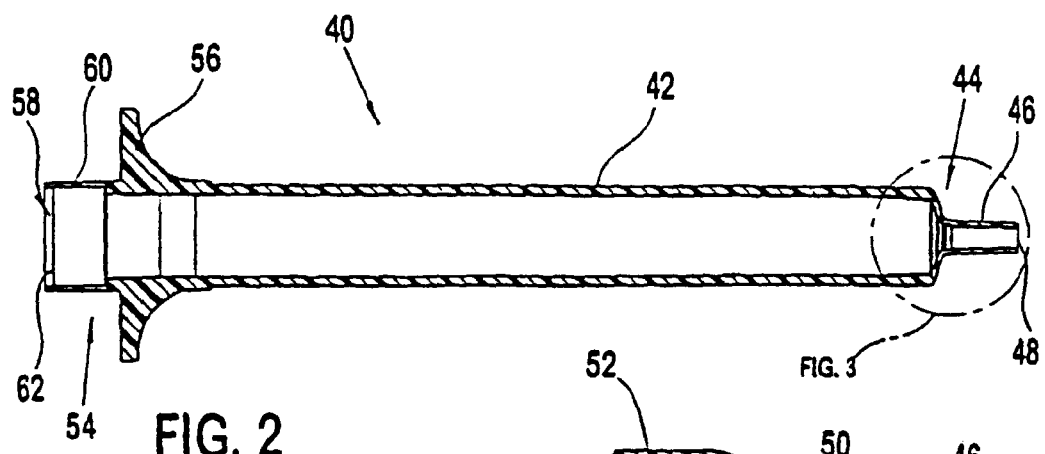
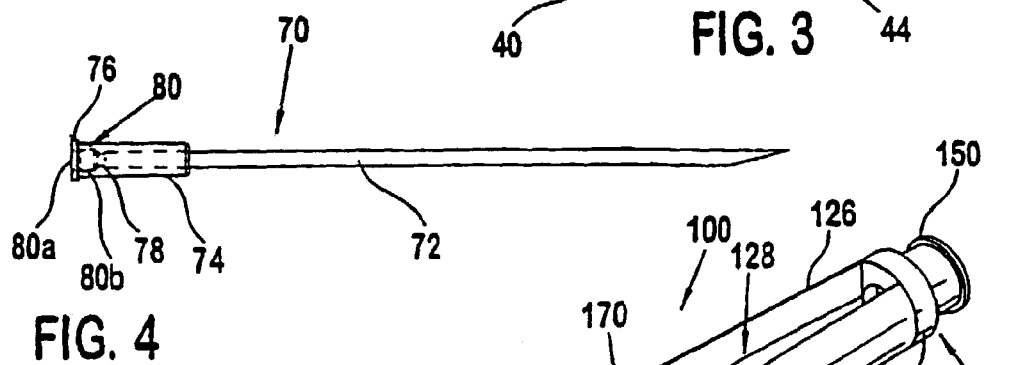
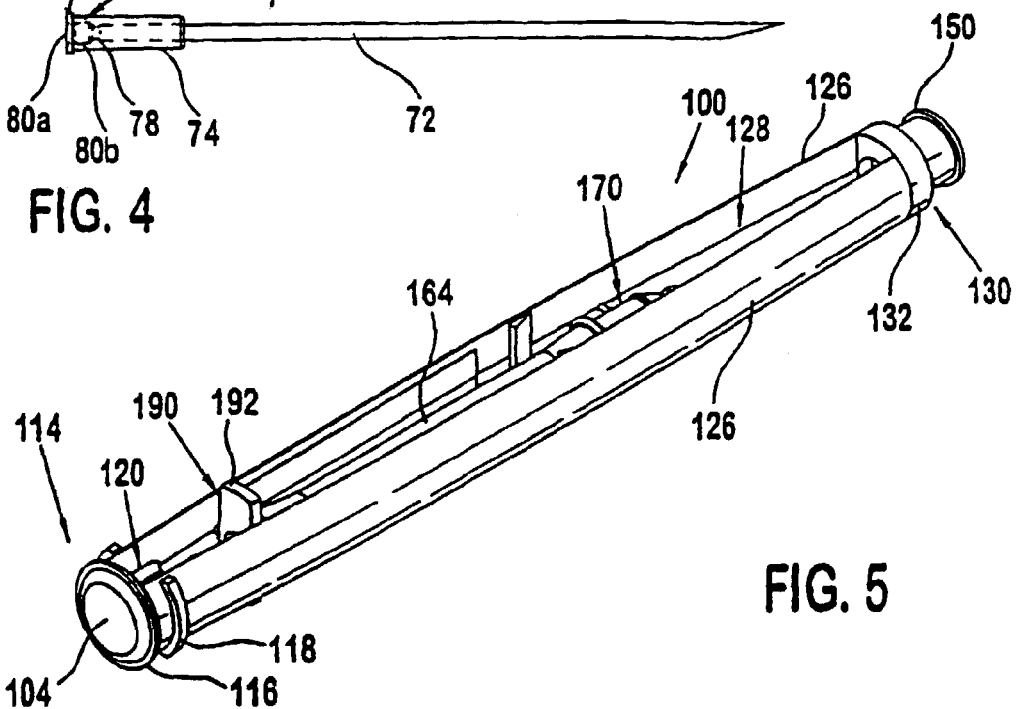

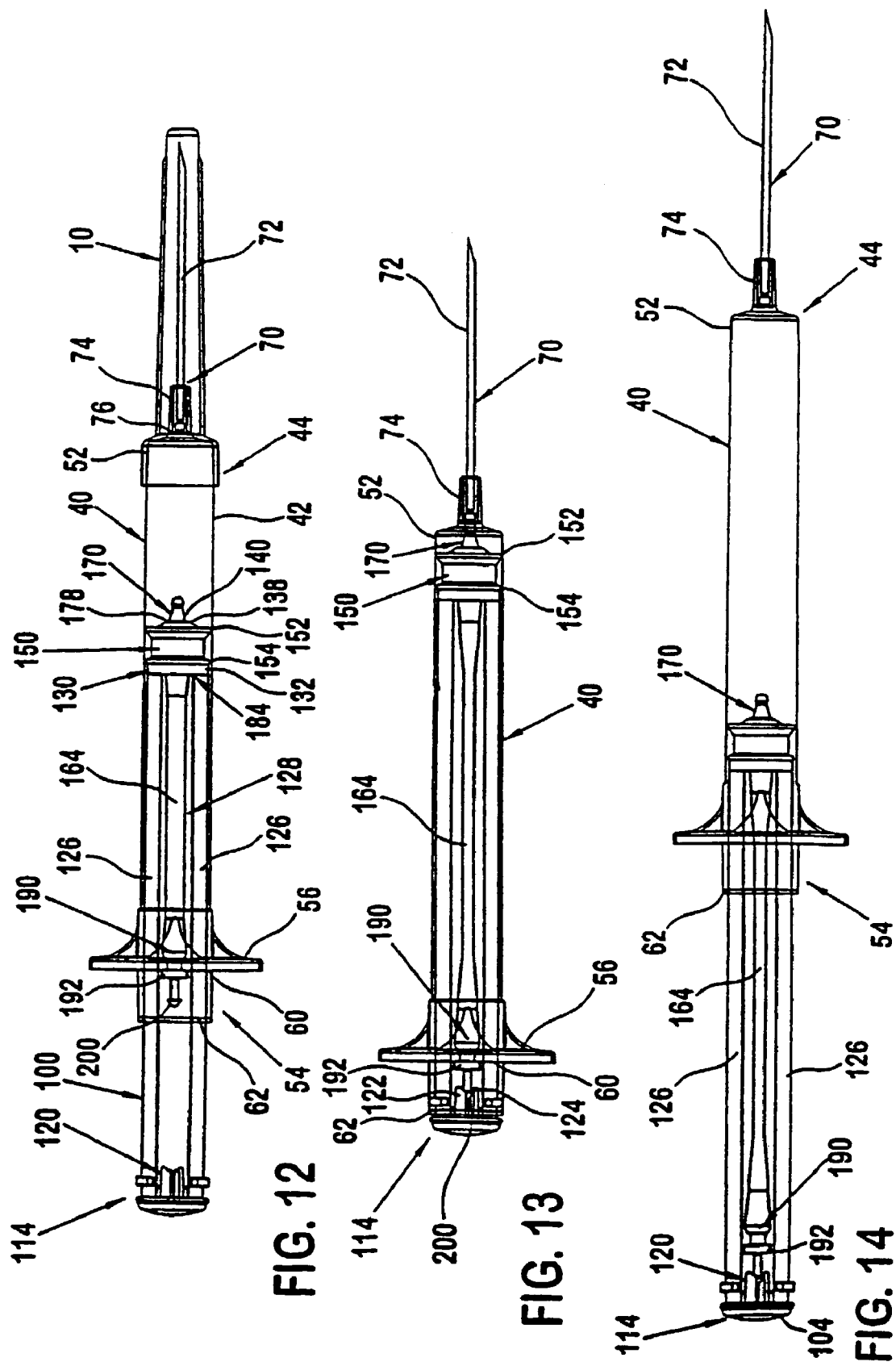

SYRINGE WITH RETRACTABLE NEEDLE ASSEMBLY

This is a continuation of PCT application PCT/US00/33897, filed Dec. 13, 2000, designating the United States, which claims continuation in part priority from PC/US99/29541, filed Dec. 13, 1999, designating the United States, the disclosures of which is incorporated herein by reference.

BACKGROUND OF THE INVENTION

The field of the present invention relates generally to apparatus for protection against an accidental sharps injury or stick from an unprotected needle.

For some time, the art has recognized the desirability of protecting personnel from accidental sharps injuries or needle sticks. More recently, concerns have been expressed about the possibility of transmitting serious or potentially fatal infection as a result of such accidents. Most recently, legislation requiring the use of safe needle technology is pending in a number of States and before the Occupation Safety and Health Administration. Although, the art has recognized the desirability of protecting against accidental sharps injuries or needle sticks, it is believed that practical protective devices are still not available.

U.S. Pat. No. 5,209,739 discloses a hypodermic needle assembly and a syringe, both having a retractable cannula. An elastomeric tube is connected between the cannula and the passage to the fluid chamber. In each of the embodiments, a separate mechanical device must be independently operated by the user to cause retraction of the cannula into a second compartment. Since the fluid must travel through the elastomeric tube to bypass the second compartment, there is a potential risk of injecting air directly into the patient if the elastomeric tube breaks.

European Patent No. 0 862 A1 discloses a device in which a needle is retracted into the syringe. In several of the embodiments, the device requires the user to independently operate a mechanical device to cause retraction of the needle. In the one embodiment which utilizes an elastic member, the elastic member is not preloaded and requires the user to depress the plunger to load the elastic member and thereafter continue to apply pressure on the plunger to avoid premature withdrawal of the plunger. As such, the device requires two hands for its operation.

Various methods of providing a preloaded retraction assembly which permit one hand operation are disclosed in co-owned PCT Application No. PCT/US97/20646, International Publication No. WO 98/20923. While these devices operate successfully, it has been found that the devices may have a somewhat reduced shelf life since the retraction member remains in a tensioned, preloaded condition.

Other devices which allow the retraction member to be loaded by the user have been introduced. However, these devices generally require a complicated or non-routine procedure to accomplish such. The further a device is from routine operation, the generally less accepted it is by the medical community. Additionally, some of these devices require a mechanical altering of the device which may be difficult to accomplish or may cause deformities which prevent the device from operating properly. See for example U.S. Pat. Nos. 5,928,200 and 5,836,917.

Furthermore, many retractable systems employ a geometrically configured retraction member which mates with a geometrically configured member of the needle assembly. A common problem associated with such is the geometrically configured retraction member is forward of the plunger sealing surface and thereby engages and seals the passageway through the needle assembly before all of the fluid is expelled. As a result, pressure builds in the syringe body. As the needle assembly retracts, a fluid passage opens and the pressurized fluid is ejected therefrom.

Another concern with prior art devices is the complicated and costly manufacturing processes. With the tremendous number of syringes and other needle devices used by the medical community, any substantial rise in cost of the products is undesirable and generally unacceptable.

Accordingly, there is a need for a syringe having an automatically retracted used needle assembly that can be used in a conventional manner and does not require elaborate manufacturing.

SUMMARY OF THE INVENTION

The present invention is directed to a syringe. The syringe includes a hollow body, a needle assembly positioned in the hollow body, and a plunger assembly in the hollow body. The needle assembly is retractable with an elastic member.

In a first separate aspect of the present invention, the syringe is actuated to put the elastic member in tension as the plunger is inserted into the hollow body.

In a second separate aspect of the present invention, the retraction member attaches to the needle assembly when the plunger is inserted substantially into the hollow body.

In a third separate aspect of the present invention, tension on the elastic member is released, thereby retracting the needle into the hollow body, after the retraction member attaches to the needle assembly.

In a fourth separate aspect of the present invention, the retention assembly holds the elastic member in tension prior to retraction as the plunger moves toward the needle assembly.

In a fifth separate aspect of the present invention, a mandrel seal moves with the retraction member prior to retraction and releasably sealingly engages the retraction member and the plunger frame.

In a sixth separate aspect of the present invention, the needle seal releasably sealingly engages the needle assembly and one end of the hollow body.

In a seventh separate aspect of the present invention, the retaining fingers releasably secure the needle assembly at one end of the hollow body.

In an eighth separate aspect of the present invention, the retaining arms releasably secure the needle seal at one end of the hollow body.

In a ninth separate aspect of the present invention, it is contemplated that combinations of the foregoing separate aspects may be incorporated into a single embodiment.

BRIEF DESCRIPTION OF THE DRAWINGS

FIG. 2 is a cross sectional view of one embodiment of the syringe barrel.

FIG. 3 is an exploded view of the closed end of the syringe barrel of FIG. 2.

FIG. 4 is a side elevation of one embodiment of the needle assembly.

FIG. 5 is an isometric view of one embodiment of a plunger assembly.

FIG. 12 illustrates an embodiment of the syringe in an assembled but unused condition.

FIG. 13 illustrates the syringe of FIG. 12 upon initial substantial depression of the plunger assembly.

FIG. 14 illustrates the syringe of FIG. 12 after loading of the syringe.

DETAILED DESCRIPTION OF THE PREFERRED EMBODIMENTS

The preferred embodiments will be described with reference to drawing figures where like numerals represent like elements throughout.

Figure 1:
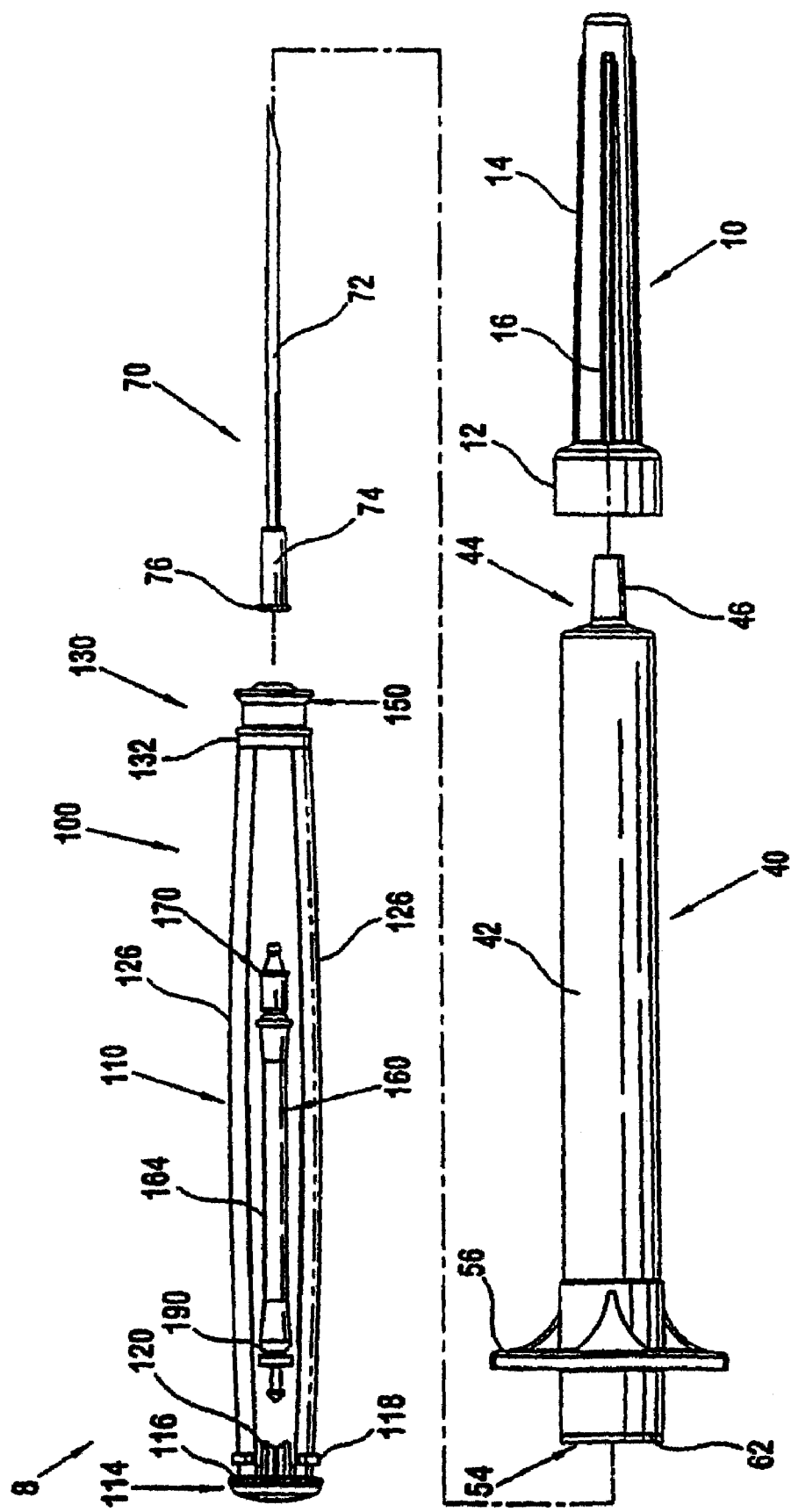
FIG. 1 is an expanded view of a syringe assembly.

With reference to FIG. 1, the syringe assembly 8 is comprised generally of the cap member 10, the syringe barrel 40, the needle assembly 70, and the plunger assembly 100.

The cap member 10 includes an open, mating end 12 and a closed cone section 14. The mating end 12 is preferably configured to slidingly engage the syringe barrel 40. Alternatively, the mating end 12 may be provided with threads (not shown) which may engage corresponding threads (not shown) on the syringe barrel 40. Other cap and corresponding barrel configurations are known and may also be employed. The closed cone section 14 preferably includes a plurality of ribs 16 which assist gripping of the cap member 10.

Referring to FIGS. 2 and 3, one embodiment of the syringe barrel 40 is comprised of a hollow body portion 42 which has a closed end 44 and an open end 54. An external stabilized grip member 56 extends from the body 42 adjacent to, but forward of the open end 54. The grip member 56 may have various configurations, the preferred elliptical configuration being shown. An internal annular shoulder 60 is defined in the hollow body 42 at approximately the same position as the grip member 56. The open end 54 defines an open cavity 58 rear of the internal annular shoulder 60. An internal annular lip 62 may also be provided adjacent the open end 54.

The closed end 44 is defined by a truncated cone 46 which includes a truncating plane having an aperture 48. Referring to FIG. 3, in one embodiment of the syringe barrel 40, a retaining groove 50 is located on the interior of the syringe barrel 40 at a position adjacent to the closed end 44. The retaining groove 50 retains the needle assembly 70 in position during use as will be described in more detail hereinafter. In one embodiment, the closed end 44 proximate the truncated cone 46 has a taper forming a generally convex rim 47 and at least one internal ramp 52, the functions of which will be described hereinafter.

Figure 3A:
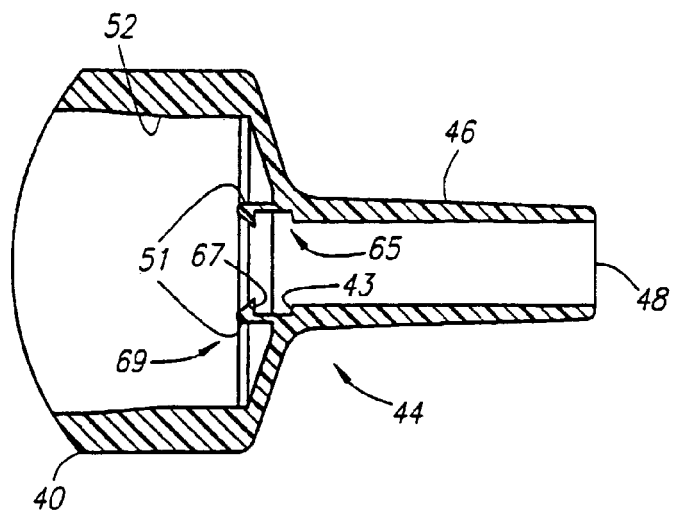
FIG. 3A is an exploded view of another embodiment of the closed end of the syringe barrel.

Referring to FIG. 3A, in another embodiment of the syringe barrel 40, retaining fingers 51 are attached to the interior of the syringe barrel 40 at a position adjacent to the closed end 44. The retaining fingers 51 retain the needle assembly 70 in position prior to retraction of the needle as will be described in more detail hereinafter.

FIG. 4 depicts one embodiment of the needle assembly 70. In this embodiment, the needle assembly 70 is comprised of a needle 72 which is centrally positioned in the conical projection 74. The conical projection 74 generally complements the interior of the truncated cone 46 of the syringe barrel 40. Immediately adjacent to the projection 74 is a sealing ring 76. The projection 74 and the sealing ring 76 preferably are formed as a unitary molding, but may be formed as separate components. The interior passage 78 of the needle assembly 70 communicates with the hollow needle 72 and the geometrically configured cavity 80 extending into the rear surface of the needle assembly 70. The cavity 80 preferably has a cylinder portion 80a and a hemispheric socket 80b which complement the geometrically configured probe 176 of the plunger mandrel 170 (shown in FIG. 10). The needle assembly 70 is positioned within the syringe barrel 40 such that the needle 72 extends through the aperture 48 and the sealing ring 76 is positioned in and retained by the retaining groove 50. Preferably, the sealing ring 76 sealingly engages the truncated cone 46 of the syringe barrel 40 and the conical projection 74.

Figure 4A:
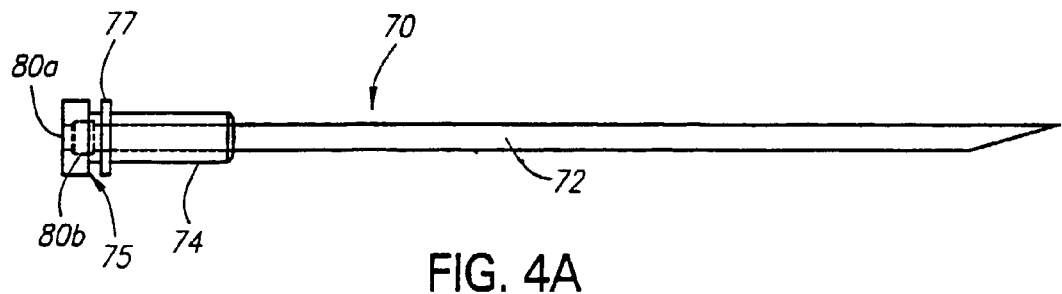
FIG. 4A is a side elevation of another embodiment of the needle assembly.

FIG. 4A depicts another embodiment of the needle assembly 70. In this embodiment, the needle assembly 70 has a needle seal lip 75 that engages and retains a needle seal 77. The needle seal lip 75 may comprise an annular collar or other surface that retains the needle seal 77. When the needle assembly 70 is inserted into the truncated cone 46 of the syringe barrel 40, the needle seal 77 is positioned between and sealingly engages the needle seal lip 75 and the closed end 44 of the syringe barrel 40. Alternately, the needle seal 77 may sealingly engage the conical projection 74 and the closed end 44 of the syringe barrel 40. To facilitate sealing engagement of the needle seal 77 with the closed end 44 of the syringe barrel 40, the closed end 44 may have a shelf 43 (shown in FIG. 3A) that engages the needle seal 77. The needle seal 77 is preferably annular, and may comprise an O-ring.

Figure 4B:
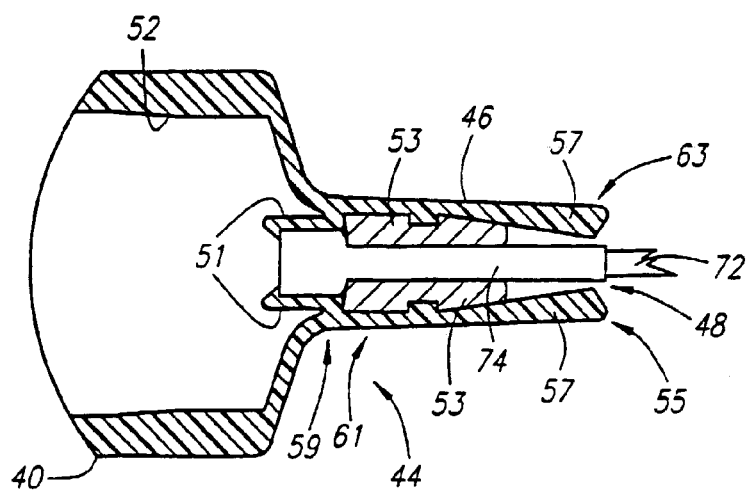
FIG. 4B is an exploded view of the closed end of another embodiment of the syringe barrel and another embodiment of the needle assembly.

Other embodiments of the syringe barrel 40 and needle assembly are shown in FIG. 4B. In these embodiments, a needle seal 53 (shown in cross-section) is inserted through the aperture 48 at the closed end 44 of the syringe barrel 40. The needle seal 53 is positioned between and sealingly engages the conical projection 74 and the truncated cone 46. In this embodiment, a smaller end 55 of the truncated cone 46 opens up to receive the needle seal 53 and then closes to retain the seal 53 in sealing engagement. To accomplish this opening and closing, the smaller end 55 of the truncated cone 46 is comprised of a plurality of retaining arms 57. A first end 61 of each retaining arm 57 is attached to a larger end 59 of the truncated cone 46. The first ends 61 are arranged about the circumference of the larger end 59. Each of the retaining arms 57 has a second end 63 that may move between an open position and a closed position when the retaining arms 57 are bent. An area defined by the second ends 63 of the retaining arms 57 while in the closed position is smaller than an area defined by the second ends 63 of the retaining arms 57 while in the open position. The area defined by the arms 57 in the closed position is smaller than a cross-sectional area of the needle seal 53 so that the needle seal 53 will not pass out through the aperture. When the needle seal retainer is in the closed position, the needle seal 53 sealingly engages the truncated cone 46 and the conical projection 74, and when the needle seal retainer is in the open position, the needle seal 53 is preferably released from sealing engagement with the truncated cone 46 and the conical projection 74. Retaining fingers 51 are attached to the interior of the syringe barrel 40 at a position adjacent to the closed end 44. The retaining fingers 51 help retain the needle assembly 70 in position prior to retraction of the needle as will be described in more detail hereinafter.

In all of the embodiments described herein, the needle assembly 70 is retained in a position that is adjacent to the closed end 44 of the barrel 40 by a needle assembly retainer prior to retraction. In the embodiments shown in FIGS. 3 and 4, the needle assembly retainer comprises the sealing ring 76 that is positioned in and retained by the retaining groove 50. In the embodiment shown in FIGS. 3A and 4B, the needle assembly retainer comprises the retaining fingers 51.

The retaining fingers 51 are preferably disposed about the circumference of a larger end 59 of the truncated cone 46. A first end 65 of each of the retaining fingers 51 is connected with the syringe barrel 40 at a location adjacent to the closed end 44. The retaining fingers 51 preferably comprise L-shaped members with a retaining lip 67 near a second end 69. The retaining fingers 51 are bendable between a closed position and an open position. While in the closed position, the second ends 69 of the fingers 51 define an area that is smaller than the area defined by the second ends 69 when they are in the open position. The smaller area defined by the fingers 51 in the closed position is smaller than a cross-sectional area of the needle assembly 70, such that the needle assembly does not pass through the needle assembly retainer when the fingers 51 are in the closed position.

Referring to FIGS. 1 and 5–11, the plunger assembly 100 includes a plunger frame 110, a retraction assembly 160, a thumb pad 104 and a sealing member 150. The plunger frame 110 includes a first end 114 and a sealing end 130 with a pair of opposed connecting rods 126 extending therebetween. The opposed connecting rods 126 define opposed retraction assembly guide tracks 128.

Figure 6:
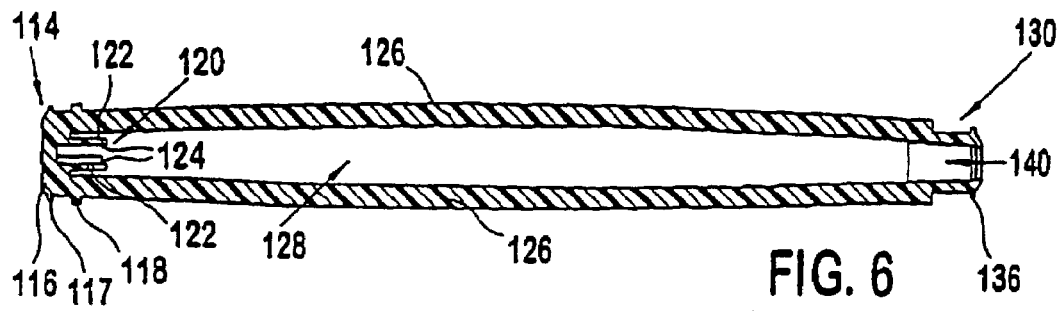
FIG. 6 is a cross sectional view of the plunger frame of the plunger assembly of FIG. 5.

As shown in FIG. 6, in one embodiment of the plunger frame, the first end 114 of the plunger frame 110 includes a terminating plate 116 extending between and bridging the opposed connecting rods 126. An annular thumb pad retaining ring 117 extends about the terminating plate 116. Additionally, a guide member 118 may extend outward from each connecting rod 126 proximate the terminating plate 116. A retention assembly 120 extends inward from the terminating plate 116 between the opposed connecting rods 126. This embodiment of the retention assembly 120 includes a pair of opposed L-shaped members 122, each L-shaped member having a hook 124 extending therefrom. Other retention assemblies which permit inward passage and then retention of a geometrically configured tip are also applicable.

Figure 6A:
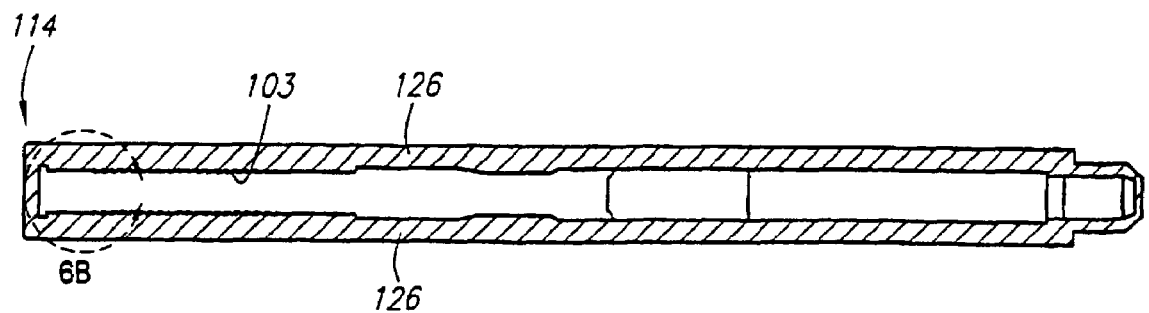
FIG. 6A is a cross sectional view of another embodiment of a plunger assembly.
Figure 6B:
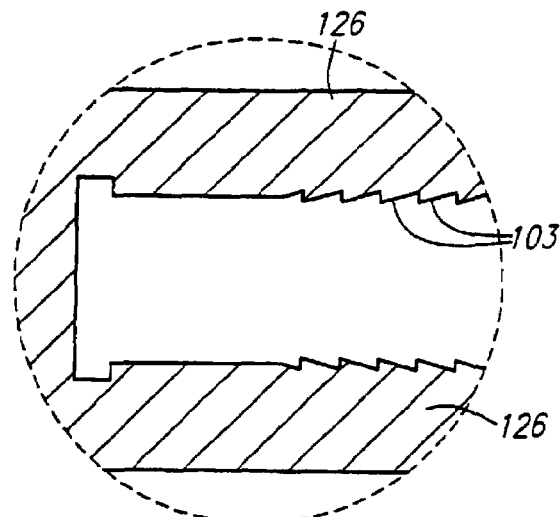
FIG. 6B is an enlarged view of part of the plunger assembly of FIG. 6A.

As shown in FIGS. 6A and 6B, another embodiment of the plunger frame has a retention assembly that comprises a plurality of retention teeth 103 arranged along a surface of the connecting rods 126 of the plunger assembly, substantially parallel to a longitudinal axis of the elongated frame portion of the plunger assembly.

Each component of the plunger frame 110 is preferably manufactured from polypropylene or glass filled polypropylene. Other materials, including various plastics, may also be used. As described in more detail hereinafter, the plunger frame 110, in addition to components of the retraction assembly 160, is preferably formed as a first shot of a multiple shot injection molding procedure.

Figure 7:
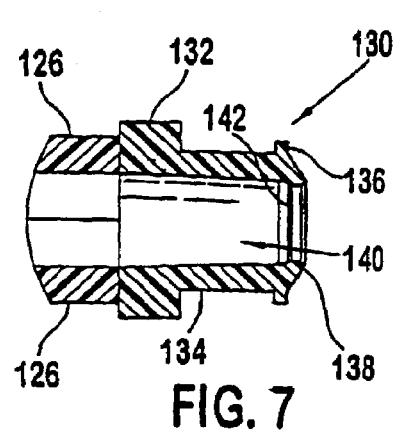
FIG. 7 is an exploded view of the sealing end of the plunger frame of FIG. 6.

As shown in FIG. 7, in one embodiment of the plunger assembly, the sealing end 130 includes a sealing platform 132 extending between the connecting rods 126 and including an apertured cylinder 134 terminating in an apertured pressure cone seat 138. The apertures are preferably concentric such that a continuous hollow integral shaft 140 passes through the sealing end 130 from the sealing platform 132 to the pressure cone seat 138. The hollow shaft 140 is preferably tapered such that the diameter is greater within the sealing platform 132 than within the pressure cone seat 138. Additionally, an internal annular ring 142 extends into the hollow shaft 140 proximate the pressure cone seat 138. An external annular retaining ring 136 is positioned about the juncture of the cylinder 134 and the pressure cone seat 138. The function of the taper and the internal and external rings 136 and 142 will be described in more detail hereinafter.

Figure 7A:
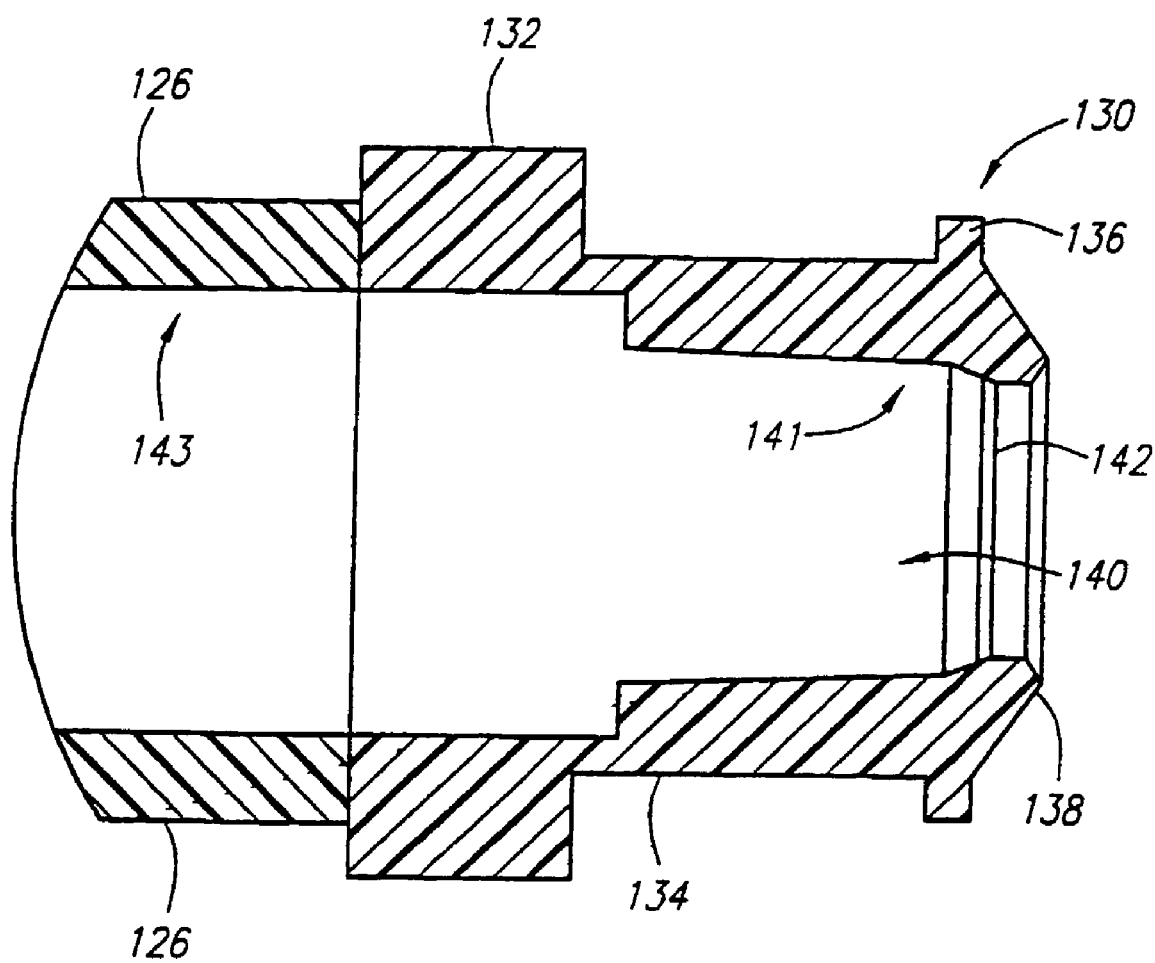
FIG. 7A is a cross sectional view of another embodiment of the sealing end of a plunger frame.

As shown in FIG. 7A, in another embodiment of the plunger assembly, the hollow shaft 140 has a first end 141 and a second end 143, wherein the first end 141 defines a cross-sectional area that is smaller than a cross-sectional area defined by the second end 143. The transition between the smaller and larger cross-sectional areas is depicted to be abrupt, but may alternately be gradual.

Figure 8:
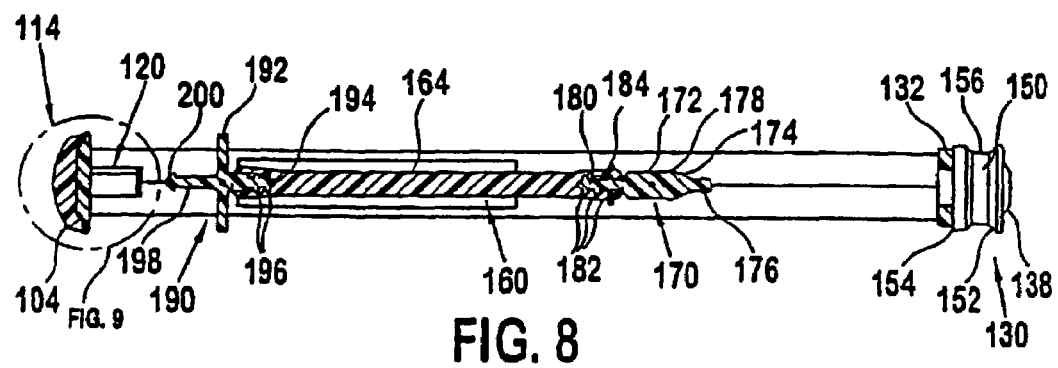
FIG. 8 is a cross sectional view of the plunger assembly of FIG. 5.

Referring to FIG. 8, the plunger sealing member 150 is positioned about the cylinder 134 and the external retaining ring 136 and is maintained in position by the external ring 136. The sealing member 150 includes annular seals 152 and 154 at each end with a narrower portion 156 positioned therebetween. When the plunger assembly 100 is positioned in the syringe barrel 40, annular seal 152 sealingly engages the inside surface of the hollow body portion 42 with an area of open space about the narrower portion 156. Annular seal 154 may also sealingly engage the hollow body 142, but may also include a passage to prevent creating a vacuum in the narrower portion 156. The sealing member 150 is preferably manufactured from an elastomer. A material found to be suitable is Kraton™ manufactured by Shell Oil.

A preferred material is Kraton™ G2706 manufactured by Shell Oil. As will be described in greater detail hereinafter, the sealing member 150 is preferably overmolded directly in position, but may be manufactured separately and subsequently positioned about the cylinder 134 and retaining ring 136.

Figure 9:
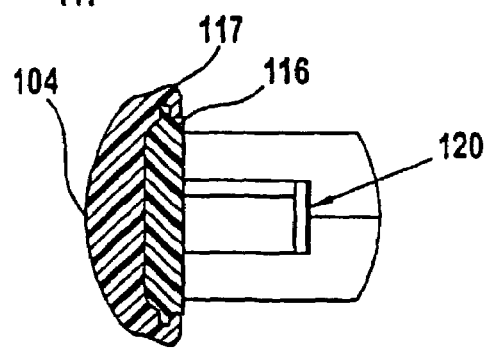
FIG. 9 is an exploded view of the first end of the plunger assembly of FIG. 8.

The first end 114 of plunger frame 110 can be utilized with the terminating plate 116 and no thumb pad 104. However, it is preferable to provide a thumb pad 104 about the terminating plate 116 and retained by the retaining ring 117 as shown in FIG. 9. The thumb pad 104 is also preferably manufactured from an elastomer, preferably Kraton™. As with the sealing member 150, it is preferable that the thumb pad 104 be overmolded directly in position, but it too may be manufactured separately and subsequently positioned and secured about the terminating plate 116.

The preferred retraction assembly 160 will be described with reference to FIGS. 5, 6C, 6D, 8, 10, 10A and 11. The retraction assembly 160 includes a retraction member 170 defined by a mandrel, a catch member 190 and an elastic member 164.

Figure 10:
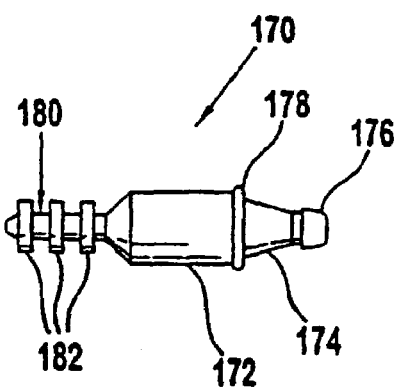
FIG. 10 is a side elevation view of one embodiment of the mandrel.

Referring to FIG. 10, one embodiment of the mandrel 170 includes a generally cylindrical body 172 with a tapered portion 174 extending from one end and a retraction member anchor 180 extending from the other. The tapered portion 174 terminates in a geometrically configured probe 176. A mandrel annular retaining ring 178 extends about the cylindrical body 172 proximate the juncture with the tapered portion 174. The mandrel 170 is releasably secured to the plunger frame by a retention means, which includes the retaining ring 178. The mandrel retaining ring 178 preferably is part of the mandrel 170 and does not separate from the mandrel 170. The retraction member anchor 180 includes a plurality of barbs 182 or the like extending therefrom for retaining the elastic member 164.

Figure 10A:
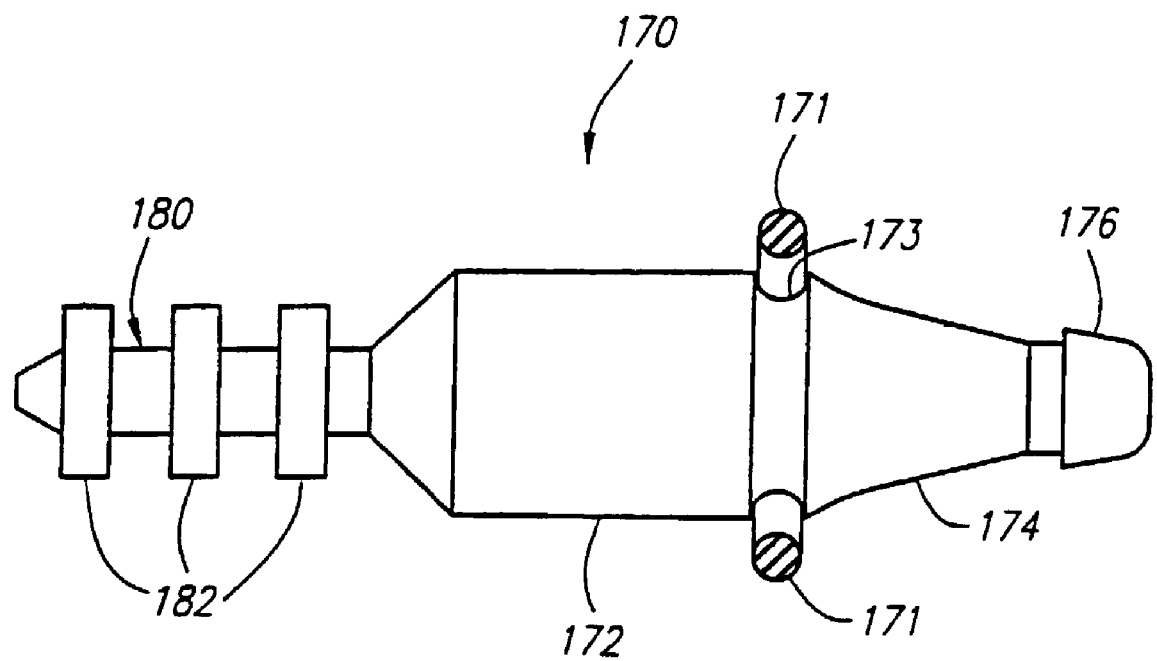
FIG. 10A is a side elevation view of another embodiment of the mandrel and a cross sectional view of the mandrel seal.

In another embodiment of the mandrel 170, as shown in FIG. 10A, the cylindrical body 172 has a groove 173 and a mandrel seal 171 (a cross-section of which is depicted) is positioned about the groove 173 between the mandrel 170 and the hollow shaft 140. The mandrel seal 171 releasably and sealingly engages the mandrel 170 and the hollow shaft 140. The mandrel seal 171 is depicted as an O-ring, but may be of any configuration that releasably and sealingly engages the hollow shaft 140 and the mandrel 170.

The mandrel seal 171 initially is in sealing engagement with the mandrel 170 and the first end 141 of the hollow shaft 140 and inhibits the passage of fluid therebetween prior to retraction of the needle. The sealing engagement creates holding forces between the hollow shaft 140 and the mandrel seal 171, as well as between the mandrel seal 171 and the mandrel 170. The holding forces inhibit movement of the seal 171 relative to the mandrel 170 and relative to the hollow shaft 140, and thus inhibit retraction of the needle. Accordingly, the retention means that releasably secures the mandrel 170 to the plunger frame includes the mandrel seal 171.

In the smaller-diameter area, the holding force between the mandrel seal 171 and the mandrel 170 is greater than the holding force between the mandrel seal 171 and the hollow shaft 140, such that the mandrel seal 171 does not move relative to the mandrel 170, but instead moves relative to the hollow shaft 140 when the mandrel 170 is moved relative to the hollow shaft 140.

The desired distribution of holding forces may provided by various means. Preferably, the mandrel 170 has an annular groove 173 about the circumference of the mandrel 170 and located at a seal position on the mandrel 170. The annular groove 173 is configured so that the mandrel seal 171 abuts or fits into the groove 173 and is held in place on the mandrel 170 at the seal position so long as the mandrel seal 171 is located in the smaller-area portion of the hollow shaft 140. Once the mandrel seal 171 moves from the smaller area to the larger area of the hollow shaft 140, the mandrel seal 171 may either remain in the groove 173 or expand away from the groove 173, as described in greater detail below.

It is noted that configurations other than a groove may also be employed to retain the mandrel seal fixed with respect to the mandrel. For example, the mandrel seal could be positioned between two annular collars on the mandrel. Additionally, any other non-smooth or irregular surface may be employed to mechanically inhibit movement of the seal relative to the mandrel. Alternately, an adhesive could be used to attach the mandrel seal to the mandrel. The mandrel seal could also be formed as an integral part of the mandrel.

Referring to FIG. 8, in one embodiment of the retraction assembly 160, an annular stop 184 extends about the cylindrical body 172 of the mandrel 170 adjacent the end of the hollow shaft 140. The stop 184 is preferably elastomeric and therefore is preferably formed in conjunction with the elastic member 164.

Figure 11:
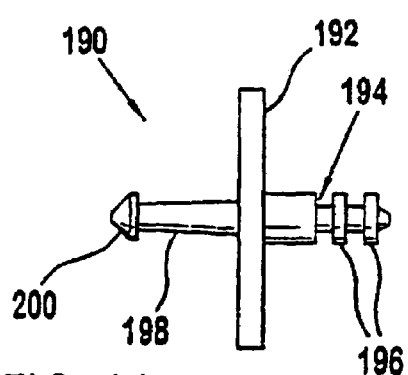
FIG. 11 is a side elevation view of one embodiment of the catch member.

Referring to FIGS. 5 and 11, one embodiment of the catch member 190 includes an elongated plate 192 which is sized such that each end of the elongated plate 192 extends into and travels within a respective retraction assembly guide track 128 of the plunger frame 110. Extending from one side of the elongated plate 192 is a catch member anchor 194 with barbs 196 or the like extending therefrom for retaining the elastic member 164. In the embodiment shown in FIG. 11, a shaft 198 extends from the opposite side of the elongated plate 192 and terminates in a geometrically configured barbed tip 200. The tip 200 is configured to mate with and be retained by the retention assembly 120 of the plunger frame 110.

Figure 6C:
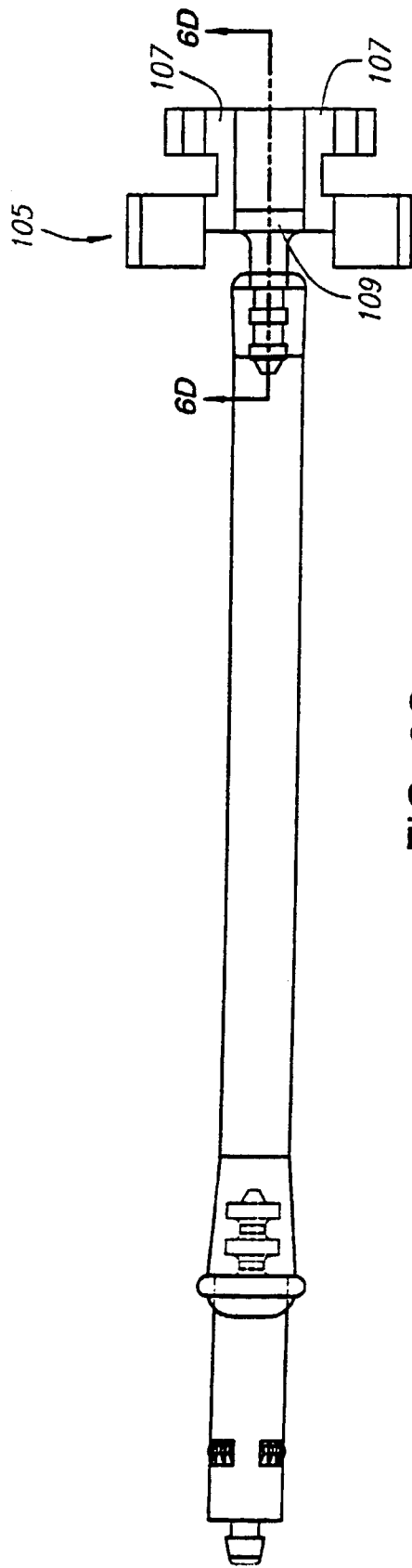
FIG. 6C is one embodiment of a retraction assembly.
Figure 6D:
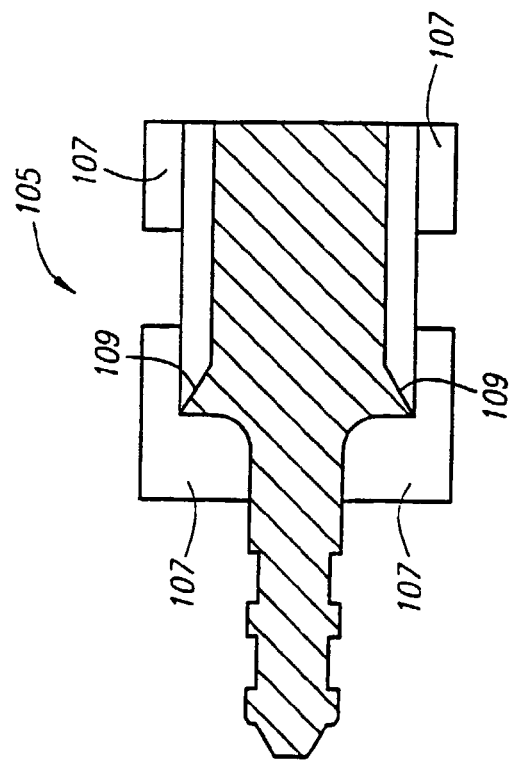
FIG. 6D is one embodiment of a catch member.

As shown in FIGS. 6C and 6D, another embodiment of the catch member 105 has a guide 107 configured to travel in the guide track 128 between the connecting rods of the plunger frame 110. The catch member 105 has a catch tooth 109 situated on either side of the catch member 105. Each catch tooth 109 engages with one of the retention teeth 103 (the retention teeth 103 are part of the retention assembly shown in FIGS. 6A and 6B) at a time. After one of the retention teeth 103 receives one of the catch teeth 109, the catch tooth 109 is inhibited from moving away from the first end 114 of the elongated frame portion. Accordingly, the catch member 105 is retained by the retention teeth 103 of the retention assembly and the elastic member 164 is thereby held in tension on one end by the sealing platform and on the other end by the catch member 105.

The mandrel 170 and the catch member 190 105 are preferably manufactured from the same material as the plunger frame 110. As such, these components can also be formed during the first shot of the multiple shot injection molding procedure used to form the plunger frame 110.

The elastic member 164 extends between the mandrel 170 and the catch member 190 105. The elastic member 164 is manufactured from a resilient material, which is preferably an elastomer, but which can be other materials, for example a stainless steel spring or the like. The elastic member 164 is preferably manufactured from Kraton™. In the preferred method of manufacture described below, the elastic member 164 is formed between the mandrel 170 and the catch member 190 105 with a second injection, overmolding shot. Do to the elastic member 164 being directly overmolded over the barbed anchors 180 and 194 and the innate bonding property of the preferred material, there is generally not a need for additional securing means, for example adhesive, to maintain the elastic member 164 secured to the mandrel 170 and catch member 190 105. It is contemplated that the elastic member 164, irrespective of the material from which it is manufactured, may also be manufactured separately and secured to the mandrel 170 and catch member 190 105. Since the sealing member 150, thumb pad 104 and stop 184 are all also preferably manufactured from the same material as the elastic member 164, they are also preferably formed during the second injection, overmolding shot.

Having described the components of the preferred syringe 8, its assembly and use will now be described with reference to FIGS. 12–19. The needle assembly 70 is positioned in the syringe barrel 40 with the needle 72 extending through the aperture 48.

In the embodiment shown in FIGS. 3 and 4, the needle assembly 70 is inserted until the sealing ring 76 seats in and is retained by the syringe body retaining groove 50.

In the embodiment shown in FIGS. 3A and 4A, the needle assembly 70 with the needle seal 77 is inserted into the truncated cone 46 of the syringe barrel 40 and is retained by the retaining fingers 51. When the needle assembly 70 is being inserted into the truncated cone 46, it contacts the retaining fingers 51. Further insertion of the needle assembly 70 moves the retaining fingers 51 into the open position so that the needle assembly 70 may pass through the opening defined by the retaining fingers 51.

When the needle assembly 70 is inserted sufficiently into the truncated cone 46, the retaining fingers 51 return to the closed position. The retaining fingers 51 are formed from an elastic material so that they return to the closed position if they are displaced from the closed position and no external forces are acting on the retaining fingers 51. If a force is applied tending to push the needle assembly 70 out of the truncated cone 46 toward the open end of the barrel 40 when the retaining fingers 51 are in the closed position, the needle assembly 70 will contact at least one of the retaining barbs 67, and at least one of the retaining fingers 51 will resist that force. The orientation of the surface of the barbs 67 in a substantially perpendicular relationship to the direction in which such a force would be applied decreases the component of the force that would act to spread the fingers 51 into the open position.

In the embodiment shown in FIG. 4B, the needle seal 53 is inserted into the truncated cone 46 through the aperture 48 rather than through the open end of the syringe barrel 40. To insert the needle seal 53 into the truncated cone 46 through the aperture 48, the retaining arms 57 are moved into the open position and held in the open position so that the needle seal 53 may pass through the opening defined by the arms 57. Once the needle seal 53 is sufficiently inserted into the truncated cone 46, the arms 57 are released and move toward the closed position. The arms 57 are formed of an elastic material so that the arms 57 return to the closed position if they are displaced from the closed position and no external forces are acting on the arms 57. Once the needle seal 53 is inserted into the truncated cone 46 and the arms 57 return to the closed position, the needle seal 53 is retained in the truncated cone 46 by the arms 57.

The needle assembly 70 may be inserted through the aperture 48 or through the open end of the barrel 40. If the needle assembly 70 is inserted through the open end of the barrel 40, it is done in the same manner as described above in 22. connection with the embodiments shown in FIGS. 3A and 4A. Accordingly, the needle assembly 70 contacts the retaining fingers 51 and pushes them into the open position. Once the needle assembly 70 is sufficiently inserted, the retaining fingers 51 move into the closed position and retain the conical projection 74 of the needle assembly 70. If the needle assembly 70 is inserted through the aperture 48, it may be inserted in the same manner as, and at the same time as, the seal 53. If inserted through the aperture 48, the retaining fingers 51 need not move to the open position to accept the needle assembly 70.

In the embodiments shown in FIGS. 3, 3A, 4, and 4A, the cap member 10 may be mated with the closed end 44 of the syringe barrel 40 either before or after insertion of the needle assembly 70. In the embodiments shown in FIG. 4B, the cap member 10 may be mated with the closed end 44 of the syringe barrel 40 after insertion of the needle seal 53.

The plunger assembly 100 is assembled by assembling the plunger frame 100, which already has the thumb pad 104 and sealing member 150 positioned thereon, and the retraction assembly 160. As explained above, the elastic member 164 is preferably molded directly to the mandrel 170 and catch member 190 105, to form the retraction assembly 160. If not formed integrally, the elastic member 164 is secured to the mandrel and catch member barbed anchors 180 and 194.

With the retraction assembly 160 complete, the mandrel 170 is inserted through the hollow shaft 140 passing through the plunger frame sealing end 130. In the embodiment shown in FIGS. 7 and 10, the mandrel 170 is inserted until the mandrel retaining ring 178 is secured by the sealing end internal annular ring 142. The mandrel retaining ring 178 forms a fluid tight seal with the plunger sealing end 130 proximate the pressure cone seat 138, thereby sealing the hollow shaft 140. The resilient stop 184 abuts against the rear surface of the sealing platform 132, thereby forming a fluid tight seal about that end of the hollow shaft 140. As the plunger assembly is withdrawn from the hollow body 42, a vacuum is created therein. The seal provided by the resilient stop 184 helps prevent air or other materials from be pulled past the mandrel 170 into the syringe body 42 by the internal vacuum force.

In the embodiment shown in FIGS. 7A and 10A, the mandrel 170 is inserted to place the mandrel seal 171 within the first end 141 of the hollow shaft 140. The mandrel seal 171 may abut a pressure cone seat 138 or a lip (not shown) on the hollow shaft 140 that inhibits excessive insertion of the mandrel 170.

With the mandrel 170 in place, the plunger assembly 100 is ready to be inserted into the syringe barrel 40 through the open end 54. The annular seals 152 and 154 sealingly engage the inside of the syringe barrel 40 as the plunger assembly 100 is inserted. The plunger assembly 100 is inserted approximately half-way into the syringe barrel 40 until the catch member 190 105 abuts the shoulder 60, as shown in FIG. 12. The syringe 8 is ready for packaging and delivery. It should be noted that at this time the elastic member 164 is not tensioned. This helps increase the shelf life of the syringe 8 since the elastic member 164 is not under constant tension. If shelf life is not a concern, the catch member 190 105 can be secured to the retention assembly 120 prior to packaging, whereby the syringe 8 would have a preloaded elastic member.

After removing the syringe assembly 8 from the packaging, the operator can hold the syringe in a typical one hand manner, i.e. with two fingers abutting the grip member 56 and the thumb on the thumb pad 104. The operator presses on the thumb pad 104 to depress the plunger assembly 100 into the syringe barrel 40 with a substantially complete depression to expel air from the syringe hollow body 42. This is similar to standard syringe operation. As the plunger assembly 100 is depressed, the catch member 190 105 is retained by the shoulder 60 such that the catch member 190 105 cannot travel forward. However, the plunger frame 110 continues its forward travel. Since the catch member 190 105 is retained but the plunger frame 110 and secured mandrel 170 continue forward, the elastic member 164 begins to stretch and tension.

As travel continues forward, the catch element 200 109 of the catch member 190 105 is received by the retention assembly 120. In the embodiment shown in FIG. 11, the catch element is a geometrically configured barbed tip 200. In the embodiment shown in FIGS. 6C and 6D, the catch element is comprised of catch teeth 109 and the retention assembly is comprised of retention teeth 103. As shown in FIG. 13 for the embodiment with a barbed tip 200, the catch element 200 is secured by the retention assembly 120 of the plunger frame 110. The elastic member 164 is thereby secured in a loaded condition between the secured mandrel 170 and the secured catch member 190 105. As the catch element 200 109 and retention assembly 120 mate, an audible "click" may occur to provide a signal of proper mating to the operator.

Additionally, the syringe barrel annular lip 62 adjacent the first end 114 of the plunger frame will discourage complete depression of the plunger assembly 100 as the catch element 200 109 is received by the retention assembly 120.

With the elastic member 164 loaded, the syringe 8 can be loaded in a typical fashion by removing the cap 10, inserting the needle 42 into a desired vial or the like, and withdrawing the plunger assembly 100 to draw up a desired dose as shown in FIG. 14. Since the elastic member 164 is tensioned between two components secured to the plunger frame 110, withdrawal of the plunger assembly 100 will not trigger the elastic member 164. Instead, the plunger assembly 100 will operate as a standard syringe plunger.

Once any air has been purged from the syringe barrel 40 in a known manner, the device 8 is ready for injection of the needle 72 into the patient. As stated above, the elastic member 164 is tensioned between two fixed components, and therefore, is not acting to move the plunger assembly 100 in either direction. As such, the user does not have to maintain constant pressure on the plunger assembly, but is free to hold the syringe 8 in the traditional dart like fashion between their thumb and forefinger of one hand, and use the other hand to pinch the patient's skin at the point of insertion for subcutaneous injection, spread the skin for intramuscular injection, and stabilize the skin for IV injection. These methods of injection are the generally preferred methods in the medical field.

Figure 15:
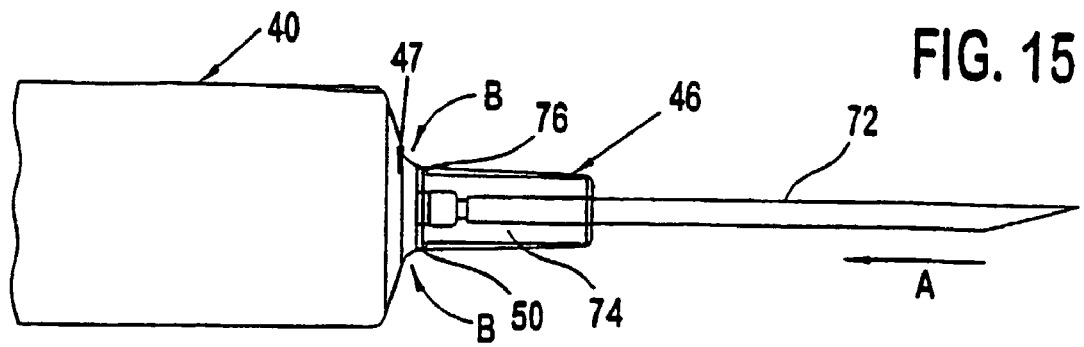
FIG. 15 illustrates the forward portion of the syringe of FIG. 12 as it is inserted in a patient.

As the needle 72 is inserted, a rearward force, indicated by the arrow A in FIG. 15, is applied against the needle assembly 70. To resist this force, the needle assembly sealing ring 76 is secured within the retaining groove 50 in the embodiment shown in FIGS. 3 and 4. Additionally, since the syringe barrel rim 47 about the truncated cone 46 is convex, the rearward force causes the syringe barrel surface to urge inward, as indicated by arrows B, thereby creating a tighter retention force about the needle assembly 70. Once the user has inserted the needle 72 into the patient, the user injects the substance into the patient by depressing the thumb pad 104. In the embodiments shown in FIGS. 3A, 4A, and 4B, the force applied against the needle assembly is resisted by the retaining fingers 51.

Figure 16:
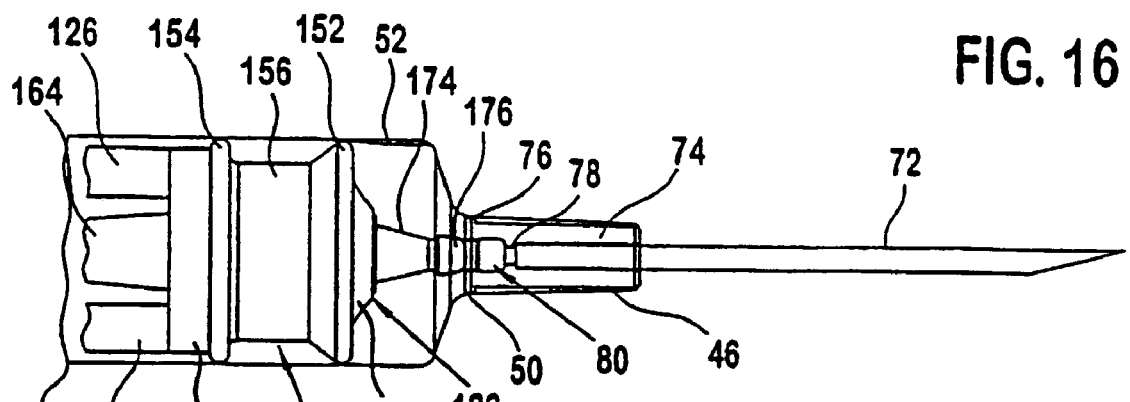
FIG. 16 illustrates the forward portion of the syringe of FIG. 12 upon substantial injection depression of the plunger assembly.

As shown in FIG. 16, upon substantial depression of the plunger assembly 100, the mandrel probe 176 begins to enter the needle assembly cavity 80. At approximately the same time, the first annular seal 152 meets and is deflected by the ramps 52 adjacent the closed end 44 of the syringe barrel 40, thereby breaking the fluid tight seal. Any fluid trapped between the plunger sealing member 150 and the needle assembly 70 is permitted to pass the deflected annular seal 152 into the open space around narrower portion 156. The second annular seal 154 may remain in sealing engagement with the syringe barrel 40 to prevent any unwanted inward or outward flow past the sealing member 150. However, the annular seal 154 may include a small passage to let trapped air about the narrower portion 156 escape.

Figure 17:
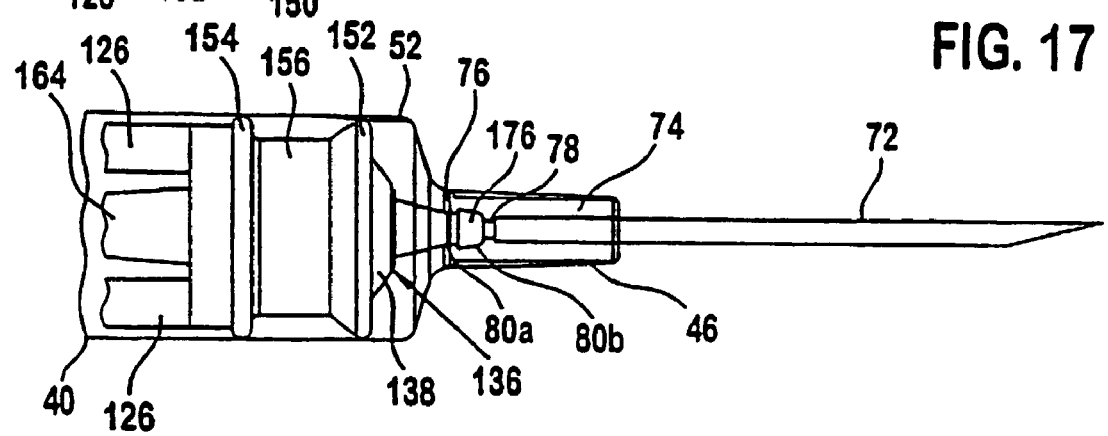
FIG. 17 illustrates the forward portion of the syringe of FIG. 12 after the mandrel tip has entered the needle assembly cavity.

The mandrel probe 176 passes through the needle assembly cavity cylindrical portion 80*a* into the geometrically configured cavity hemispherical socket 80*b* whereby the mandrel 170 is secured to the needle assembly 70 as shown in FIG. 17.

At approximately the same time the mandrel 170 and needle assembly 70 attach, the retaining fingers 51 are moved into the open position by the plunger assembly 100 so that the needle assembly 70 may pass through the opening defined by the fingers 51. A holding force exerted by the fingers 51 on the needle assembly 70 is lower when the fingers 51 are in the open position than when the fingers 51 are in the closed position. The tension in the elastic member is sufficient to overcome any remaining holding force exerted by the fingers 51 on the needle assembly 70.

Once the mandrel 170 is secured to the needle assembly 70 as shown in FIG. 17, the mandrel probe 176 has moved as far into the needle assembly 70 as possible, yet the plunger frame 110 has not completed its full stroke. As such, continued force on the thumb pad 104 will continue to move the plunger frame 110 forward. Since the mandrel 170 position is fixed and the plunger frame 110 is being forced forward, the mandrel is pushed backward.

Figure 18:
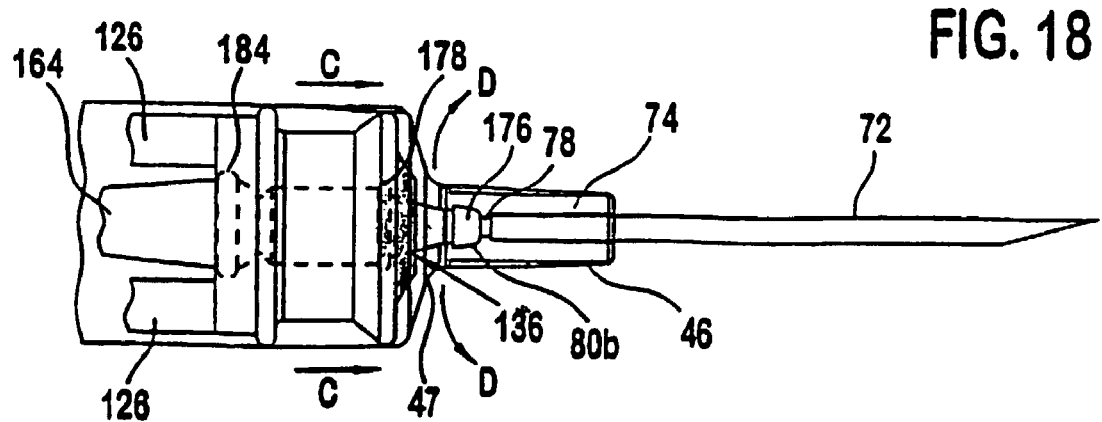
FIG. 18 illustrates the forward portion of the syringe of FIG. 12 upon complete depression of the plunger assembly.

In the embodiment shown in FIGS. 7 and 10, the retaining ring 178 will be forced inward past the plunger sealing end retaining ring 136, thereby releasing the mandrel 170 as shown in FIG. 18. That is, the mandrel retaining ring 178 moves behind the retaining ring 136 as shown in phantom.

In the embodiments shown in FIGS. 7A and 10A, as the needle user continues depressing the plunger, the plunger frame continues moving forward relative to the mandrel 170, so that the mandrel 170 is moved from a first position in the smaller-area first end 141 of the hollow shaft 140 to a second position in the larger-area second end 143 of the hollow shaft 140.

As the mandrel 170 moves from the first position toward the second position, the holding force between the hollow shaft 140 and the mandrel seal 171 is overcome and the mandrel seal 171 slides against the hollow shaft 140. The mandrel seal 171 moves with the mandrel 170 because the holding force between the mandrel seal 171 and the mandrel 170 is greater than the holding force between the mandrel seal 171 and the hollow shaft 140.

Once the mandrel seal 171 moves into the larger area of the second end 143 of the hollow shaft 140, the mandrel seal 171 either expands away from the mandrel 170 or remains engaged with the mandrel 170. The seal 171 would expand if it were compressed around the mandrel 170 by the hollow shaft 140 during the assembly of the syringe. If the seal 171 expands, the area defined by an opening in the seal 171 (the inner seal area) preferably becomes large enough as the seal 171 moves from the first position to the second position, such that the mandrel 170 may retract the needle through the inner seal area.

In any case, the mandrel seal 171 no longer secures the mandrel 170 to the hollow shaft 140 after the mandrel seal 171 moves from the first position to the second position within the hollow shaft 140.

Figure 19:
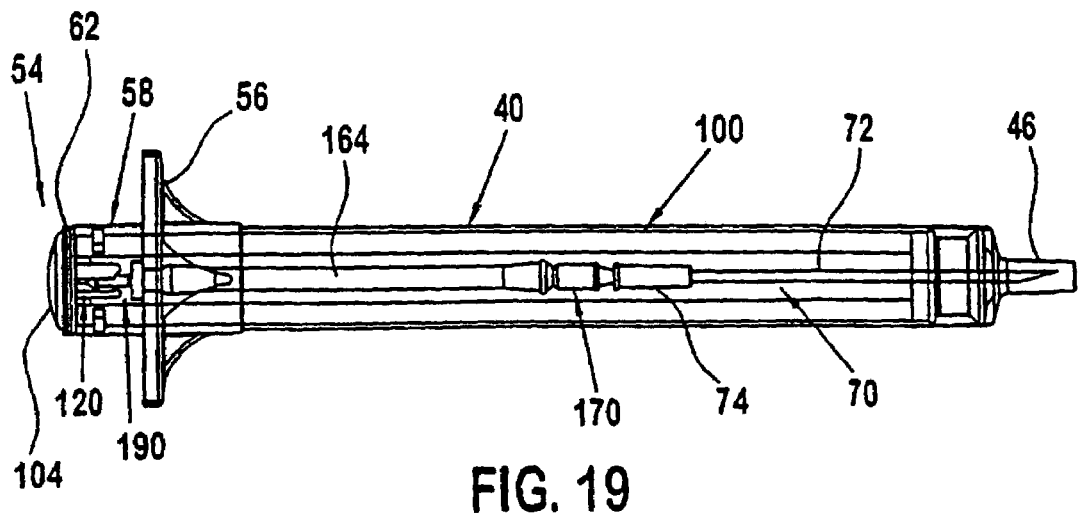
FIG. 19 illustrates the syringe of FIG. 12 after retraction of the needle.

Since the mandrel 170 is under the load of the elastic member 164 but no longer secured to the hollow shaft 140, the load of the elastic member 164 automatically retracts the mandrel 170 into the plunger frame 110 between the connecting rods 126. Through the connection of mandrel probe 176 and the geometrically configured needle assembly cavity 80, the needle assembly 70 is also retracted into the plunger frame 110, as shown in FIG. 19.

In one embodiment, the tapered pressure cone seat 138 on the sealing end of the plunger frame 110 contacts the convex, tapered rim 47 of cone 46 and causes it to spread slightly. This reduces the retaining force of cone 46 on the needle assembly 70 to assist retraction of the needle assembly 70. Furthermore, since the tapered rim 47 is convex, the forward fluid and plunger force, as indicated by arrow C in FIG. 18, urge the tapered rim 47 outward, as indicated by arrows D, further easing the retaining force and thereby reducing the requisite retraction force. This flexing preferably occurs simultaneously or slightly after the mandrel probe 176 enters the hemispherical portion 80a of the needle assembly cavity 80.

Referring again to FIG. 19, as the plunger assembly 100 completes its stroke, the thumb pad 104 enters the open cavity 58 at the end of the syringe barrel 40. In the preferred embodiment, the thumb pad 104 is manufactured from a resilient material which sealingly engages the syringe barrel 40 wall, thereby closing the open end 54 and preventing any inadvertent fluid flow out of the syringe barrel 40. Additionally, since the thumb pad 104 enters and is recessed in the open cavity 58, it makes it difficult for anyone to inadvertently or intentionally remove the plunger assembly 100 and expose the used needle 72. The thumb pad 104 preferably has a semi-domed configuration which enhances its inaccessibility. Additionally, the thumb pad 104 is preferably inserted past the inner annular lip 62 and retained thereby, further enhancing inaccessibility.

Figure 20:
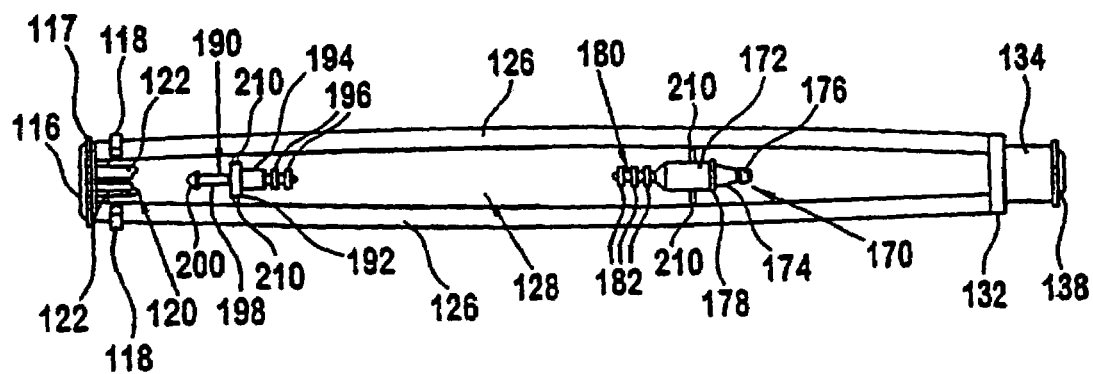
FIG. 20 shows the plunger assembly members formed from the first injection mold shot in accordance with the preferred method of manufacture.
Figure 21:
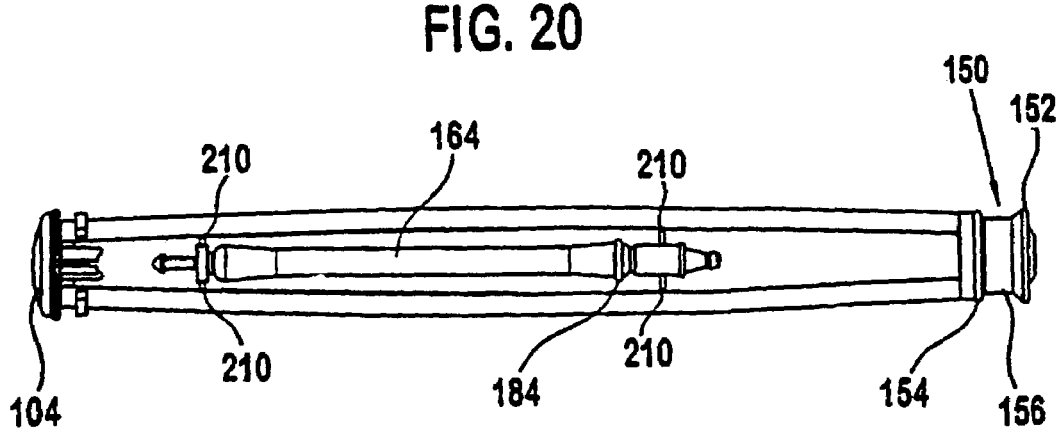
FIG. 21 shows the plunger assembly as formed from the second injection overmold shot in accordance with the preferred method of manufacture.

The method of manufacture of one embodiment of the syringe will now be described with reference to FIGS. 20 and 21. A first shot injection mold procedure is utilized to form the plunger frame 110 components (the first end 114, the sealing end 130 and the connecting rods 126 extending therebetween), the mandrel 170, and the catch member 190 105 in a single shot of the desired material, in the preferred embodiment, polypropylene. The resultant component is shown in FIG. 20. The mandrel 170 and the catch member 190 105 are maintained in position relative to one another and the plunger frame 110 by runners 210 extending from the components 170 and 190 to the connecting rods 126. The formed plunger frame 110, mandrel 170 and catch member 190 105 are then positioned in a second mold cavity. Using a second injection, overmold shot of the desired material, in the preferred embodiment, Kraton™, the elastic member 164, stop 184, sealing member 150 and thumb pad 104 are formed directly over the corresponding parts of the plunger frame 110, mandrel 170 and catch member 190 105 as shown in FIG. 21. After the plunger assembly 100 is removed from the second mold, the runners 210 are trimmed off the mandrel 170 and connecting rods 126, thereby freeing the mandrel 170. The mandrel 170 is then pushed through the plunger sealing end hollow shaft 140 until it is retained in position by the interaction of the mandrel retaining ring 178 and the plunger sealing end retaining ring 136. After the mandrel 170 is secured, the runners 210 can be trimmed between the catch member 190 105 and the connecting rods 126. While it is possible to trim all of the runners 210 at the same time, it is preferable to maintain the runners 210 supporting the catch member 190 105 to avoid excessive movement of the retraction assembly 160 during insertion of the mandrel 170. Once the mandrel 170 is inserted and the runners 210 are trimmed, the plunger assembly 100 is ready for use in accordance with the above.

This method of overmolding a resilient, elastomeric material about a frame assembly is also contemplated for use in forming various other medical and non-medical articles. With respect to medical articles, retractable blood collection devices, automated lancets, syringes with tensioned or tensionable elastomeric inner or outer sheaths, and butterfly devices are among the articles considered.

While the present invention has been described in terms of the preferred embodiments, other variations which are within the scope of the invention as defined in the claims will be apparent to those skilled in the art.

We claim:

1. A syringe comprising
   a hollow body including a substantially closed end that defines an aperture, a substantially open end and an internal shoulder;
   a needle assembly in the hollow body including a needle extendable through the aperture;
   a plunger assembly movable in the hollow body including an elongate portion extending through the substantially open end from the hollow body, a sealing platform at one end of the elongate portion within the hollow body and a retraction member releasably secured to the sealing platform and engageable with the needle assembly;
   a catch member engageable with the internal shoulder and selectively engageable with the plunger assembly while engaged with the shoulder;
   an elastic member extending between the retraction member and the catch member.

2. The syringe of claim 1, the elongate portion defining at least one longitudinally extending guide track, the catch being slideably retained in the longitudinally extending guide track.

3. The syringe of claim 1, the plunger assembly further including a retention assembly distant the sealing platform configured to engage the catch member to restrain the catch member against movement in the guide track.

4. The syringe of claim 3, the retention assembly having at least one hook, the catch member including a barbed tip engageable with the at least one hook.

5. The syringe of claim 4, the retention assembly further having a plurality of hooks defining a socket for receipt and retention of the barbed tip.

6. The syringe of claim 3, the retention assembly further having at least one retention tooth and the catch member including a least one catch tooth engageable with the at least one retention tooth.

7. The syringe of claim 6, the retention assembly further having retention teeth spaced longitudinally of the elongate portion.

8. The syringe of claim 1, the sealing platform having a hollow shaft, the retraction member being in sealing engagement with the hollow shaft prior to retraction.

9. The syringe of claim 8, the retraction member having a circumferential groove about the outer periphery and an O-ring seal in the groove, the hollow shaft having a seat receiving the seal.

10. The syringe of claim 1, the sealing platform having a first annular seal distant the elongate portion and a second annular seal proximate the elongate portion spaced apart by a recessed area, each annular seal sealingly engaging the hollow body.

11. The syringe of claim 10, the hollow body further including at least one ramp member proximate the substantially closed end engageable with the first annular seal with the plunger assembly proximate the substantially closed end of the hollow body breaking the sealing engagement of the first annular seal with the hollow body.

12. The syringe of claim 1, the elongate portion including a thumb pad, the thumb pad being in sealing engagement with the hollow body with the sealing platform against the substantially closed end of the hollow body.

13. The syringe of claim 1, the substantially closed end of the hollow body having a truncated cone receiving the needle assembly and a convex rim about the truncated cone.

14. The syringe of claim 13, the sealing platform including a pressure cone on the end of the plunger assembly facing the substantially closed end engageable with the convex rim about the truncated cone.

15. The syringe of claim 1, the substantially closed end of the hollow body having a truncated cone, the needle assembly being positionable in the truncated cone, a needle assembly retainer proximate the substantially closed end of the hollow body releaseably securing the needle assembly in the truncated cone.

16. The syringe of claim 15, the needle assembly retainer having a retaining finger.

17. The syringe of claim 15, the needle assembly retainer having a plurality of retaining fingers disposed about a circumference of a larger end of the truncated cone, the proximal end of each of the retaining fingers being attached to the hollow body.

18. The syringe of claim 17, each of the retaining fingers having a barb on the distal end of the finger, the fingers each being bendable between an engage position and a disengage position.

19. The syringe of claim 18, the plunger assembly further including a pressure cone engageable with the distal ends of the fingers.

20. The syringe of claim 1, the retraction member having a probe and the needle assembly further including a socket resistively receiving the probe.

21. A syringe comprising
a hollow body including a substantially closed end that defines an aperture and a substantially open end;
a needle assembly in the hollow body including a needle extendable through the aperture;
a plunger assembly movable in the hollow body including an elongate portion extending through the substantially open end from the hollow body, a sealing platform at one end of the elongate portion within the hollow body and a retraction member releasably secured to the sealing platform and engageable with the needle assembly, the sealing platform having a hollow shaft, the retraction member being in sealing engagement with the hollow shaft prior to retraction, the retraction member having a circumferential groove about the outer periphery and an O-ring seal in the groove, the hollow shaft having a seat receiving the seal;
an elastic member engaged with the retraction member.

22. The syringe of claim 21, the sealing platform having a first annular seal distant the elongate portion and a second annular seal proximate the elongate portion spaced apart by a recessed area, each annular seal sealingly engaging the hollow body.

23. The syringe of claim 22, the hollow body further including at least one ramp member proximate the substantially closed end engageable with the first annular seal with the plunger assembly proximate the substantially closed end of the hollow body breaking the sealing engagement of the first annular seal with the hollow body.

24. The syringe of claim 21, the elongate portion including a thumb pad, the thumb pad being in sealing engagement with the hollow body with the sealing platform against the substantially closed end of the hollow body.

25. The syringe of claim 21, the substantially closed end of the hollow body having a truncated cone receiving the needle assembly and a convex rim about the truncated cone.

26. The syringe of claim 25, the sealing platform including a pressure cone on the end of the plunger assembly facing the substantially closed end engageable with the convex rim about the truncated cone.

27. The syringe of claim 21, the substantially closed end of the hollow body having a truncated cone, the needle assembly being positionable in the truncated cone, a needle assembly retainer proximate the substantially closed end of the hollow body releaseably securing the needle assembly in the truncated cone.

28. The syringe of claim 27, the needle assembly retainer having a retaining finger.

29. The syringe of claim 27, the needle assembly retainer having a plurality of retaining fingers disposed about a circumference of a larger end of the truncated cone, the proximal end of each of the retaining fingers being attached to the hollow body.

30. The syringe of claim 29, each of the retaining fingers having a barb on the distal end of the finger, the fingers each being bendable between an engage position and a disengage position.

31. The syringe of claim 30, the plunger assembly further including a pressure cone engageable with the distal ends of the fingers.

32. The syringe of claim 21, the retraction member having a probe and the needle assembly further including a socket resistively receiving the probe.

33. A syringe comprising
a hollow body including a substantially closed end that defines an aperture, a substantially open end and at least one ramp member proximate the substantially closed end;
a needle assembly in the hollow body including a needle extendable through the aperture;
a plunger assembly movable in the hollow body including an elongate portion extending through the substantially open end from the hollow body, a sealing platform at one end of the elongate portion within the hollow body and a retraction member releasably secured to the sealing platform and engageable with the needle assembly, the sealing platform having a first annular seal distant the elongate portion and a second annular seal proximate the elongate portion spaced apart by a recessed area, each annular seal sealingly engaging the hollow body, the at least one ramp member engageable with the first annular seal with the plunger assembly proximate the substantially closed end of the hollow body breaking the sealing engagement of the first annular seal with the hollow body;
an elastic member engaged with the retraction member.

34. The syringe of claim 33, the elongate portion including a thumb pad, the thumb pad being in sealing engagement with the hollow body with the sealing platform against the substantially closed end of the hollow body.

35. The syringe of claim 33, the substantially closed end of the hollow body having a truncated cone receiving the needle assembly and a convex rim about the truncated cone.

36. The syringe of claim 35, the sealing platform including a pressure cone on the end of the plunger assembly facing the substantially closed end engageable with the convex rim about the truncated cone.

37. The syringe of claim 33, the substantially closed end of the hollow body having a truncated cone, the needle assembly being positionable in the truncated cone, a needle assembly retainer proximate the substantially closed end of the hollow body releaseably securing the needle assembly in the truncated cone.

38. The syringe of claim 37, the needle assembly retainer having a retaining finger.

39. The syringe of claim 37, the needle assembly retainer having a plurality of retaining fingers disposed about a circumference of a larger end of the truncated cone, the proximal end of each of the retaining fingers being attached to the hollow body.

40. The syringe of claim 39, each of the retaining fingers having a barb on the distal end of the finger, the fingers each being bendable between an engage position and a disengage position.

41. The syringe of claim 40, the plunger assembly further including a pressure cone engageable with the distal ends of the fingers.

42. The syringe of claim 33, the retraction member having a probe and the needle assembly further including a socket resistively receiving the probe.

43. A syringe comprising
a hollow body including a substantially closed end that defines an aperture, and a substantially open end;
a needle assembly in the hollow body including a needle extendable through the aperture;
a plunger assembly movable in the hollow body including an elongate portion extending through the substantially open end from the hollow body, a sealing platform at one end of the elongate portion within the hollow body and a retraction member releasably secured to the sealing platform and engageable with the needle assembly, the elongate portion including a thumb pad, the thumb pad being in sealing engagement with the hollow body with the sealing platform against the substantially closed end of the hollow body;
an elastic member engaged with the retraction member.

44. A syringe comprising
a hollow body including a substantially closed end that defines an aperture, a substantially open end and an internal shoulder;
a needle assembly in the hollow body including a needle extendable through the aperture;
a plunger assembly movable in the hollow body including an elongate portion extending through the substantially open end from the hollow body, a sealing platform at one end of the elongate portion within the hollow body and a retraction member releasably secured to the sealing platform and engageable with the needle assembly;
a catch member engageable with the internal shoulder and selectively engageable with the plunger assembly while engaged with the shoulder, the elongate portion defining at least one longitudinally extending guide track, the catch being slideably retained in the longitudinally extending guide track, the plunger assembly further including a retention assembly distant the sealing platform configured to engage the catch member to restrain the catch member against movement in the guide track, the retention assembly having at least one hook, the catch member including a barbed tip engageable with the at least one hook;
an elastic member extending between the retraction member and the catch member.

45. The syringe of claim 45, the retention assembly further having a plurality of hooks defining a socket for receipt and retention of the barbed tip.

46. A syringe comprising
a hollow body including a substantially closed end that defines an aperture, a substantially open end and an internal shoulder;
a needle assembly in the hollow body including a needle extendable through the aperture;
a plunger assembly movable in the hollow body including an elongate portion extending through the substantially open end from the hollow body, a sealing platform at one end of the elongate portion within the hollow body, a retention assembly distant the sealing platform and having at least one retention tooth and a retraction member releasably secured to the sealing platform and engageable with the needle assembly, the elongate portion defining at least one longitudinally extending guide track;
a catch member engageable with the internal shoulder and selectively engageable with the plunger assembly while engaged with the shoulder, the catch being slideably retained in the longitudinally extending guide track, the retention assembly configured to engage the catch member to restrain the catch member against movement in the guide track the catch member including a least one catch tooth engageable with the at least one retention tooth;
an elastic member extending between the retraction member and the catch member.

47. The syringe of claim 46, the retention assembly further having retention teeth spaced longitudinally of the elongate portion.

48. A syringe comprising
a hollow body including a substantially closed end that defines an aperture, a substantially open end and an internal shoulder;
a needle assembly in the hollow body including a needle extendable through the aperture;
a plunger assembly movable in the hollow body including an elongate portion extending through the substantially open end from the hollow body, a sealing platform at one end of the elongate portion within the hollow body and a retraction member releasably secured to the sealing platform and engageable with the needle assembly and having a retraction member anchor extending from one end;
a catch member engageable with the internal shoulder and selectively engageable with the plunger assembly while engaged with the shoulder and having a catch member anchor;
an elastic member extending between the retraction member and the catch member and being a cord molded about the retraction member anchor at the first end and about the catch member anchor at the second end.

49. The syringe of claim 48, the elongate portion defining at least one longitudinally extending guide track, the catch being slideably retained in the longitudinally extending guide track.

50. The syringe of claim 48, the plunger assembly further including a retention assembly distant the sealing platform configured to engage the catch member to restrain the catch member against movement in the guide track.

51. The syringe of claim 50, the retention assembly having at least one hook, the catch member including a barbed tip engageable with the at least one hook.

52. The syringe of claim 51, the retention assembly further having a plurality of hooks defining a socket for receipt and retention of the barbed tip.

53. The syringe of claim 50, the retention assembly further having at least one retention tooth and the catch member including a least one catch tooth engageable with the at least one retention tooth.

54. The syringe of claim 53, the retention assembly further having retention teeth spaced longitudinally of the elongate portion.

* * * * *